United States Patent [19]

Fleming et al.

[11] 4,164,447

[45] Aug. 14, 1979

[54] O-TRANSCARBAMOYLASE

[75] Inventors: Ian D. Fleming, Chalfont St. Peter; Michael K. Turner, Wembley; Stephen J. Brewer, High Wycombe, all of England

[73] Assignee: Glaxo Laboratories Limited, Greenford, England

[21] Appl. No.: 854,032

[22] Filed: Nov. 22, 1977

Related U.S. Application Data

[62] Division of Ser. No. 768,945, Feb. 15, 1977, Pat. No. 4,075,061.

[30] Foreign Application Priority Data

Feb. 19, 1976 [GB] United Kingdom ............... 6623/76

[51] Int. Cl.$^2$ .......................................... C12D 13/10
[52] U.S. Cl. ................................................... 435/173
[58] Field of Search .................... 195/62, 66 R, 63, 68

[56] References Cited

U.S. PATENT DOCUMENTS

| | | | |
|---|---|---|---|
| 3,862,004 | 1/1975 | Takabashi et al. ............ | 195/36 C X |
| 3,914,158 | 10/1975 | Stapley et al. ..................... | 195/80 R |
| 3,976,546 | 8/1976 | Smith et al. ............................ | 195/29 |
| 3,985,742 | 10/1976 | Stapley et al. ................. | 195/80 R X |

FOREIGN PATENT DOCUMENTS 2224640 8/1973 Fed. Rep. of Germany ........ 195/36 C

OTHER PUBLICATIONS

Enzyme Nomenclature; International Union of Pure and Applied Chemistry and the International Union of Biochemistry, pp. 128 and 129, 1973.

*Primary Examiner*—Raymond N. Jones
*Assistant Examiner*—Robert J. Warden
*Attorney, Agent, or Firm*—Bacon & Thomas

[57] ABSTRACT

A novel O-transcarbamoylase enzyme and its use in preparing a variety of 3-carbamoyloxymethyl cephalosporins from 3-hydroxymethyl cephalosporins and carbamoyl compounds are described.

6 Claims, No Drawings

O-TRANSCARBAMOYLASE

This is a division of application Ser. No. 768,945, filed Feb. 15, 1977 now U.S. Pat. No. 4,075,061.

This invention is concerned with improvements in or relating to enzymes and their use in semi-synthetic antibiotic production. More particularly, the invention is concerned with an O-transcarbamoylase and its use in producing 3-carbamoyloxymethyl cephalosporin antibiotics.

One class of semi-synthetic cephalosporin antibiotics which has attracted considerable interest comprises compounds having a carbamoyloxymethyl i.e. —CH$_2$OCONH$_2$ group, at the 3-position of the cephalosporin nucleus, and a number of antibiotics of this type, possessing a variety of 7$\beta$-acylamido groups, have been proposed. Although fermentation methods exist whereby 3-carbamoyloxymethyl cephalosporins may be produced, such methods have the disadvantage that mixtures are obtained. The individual compounds of such mixtures generally require further chemical modification after separation, and such chemical modifications may be difficult to carry out.

The preparation of 3-carbamoyloxymethyl cephalosporin compounds from 3-hydroxymethyl cephalosporin compounds is, however, an attractive proposition because the latter compounds can be produced in good yield, for example by the method of Belgian Pat. No. 814937. These 3-hydroxymethyl cephalosporin compounds can be reacted with chemical reagents, e.g. isocyanates, to produce 3-carbamoyloxymethyl cephalosporin compounds, but the reagents so far proposed possess various disadvantages, including instability and the hazardous nature of the starting materials required for their preparation.

We have now discovered the existence of an O-transcarbamoylase which is an enzyme capable of transferring a carbamoyl group (NH$_2$CO—) to a 3-hydroxymethyl cephalosporin to produce a 3-carbamoyloxymethyl cephalosporin, this enzyme being produced by a microbial source.

Thus, according to an aspect of the invention, we provide an O-transcarbamoylase of microbial origin which is capable of transferring a carbamoyl group to a 3-hydroxymethyl cephalosporin to produce a 3-carbamoyloxymethyl cephalosporin, and which is partially or completely free from deleterious enzymes.

N-transcarbamoylases have previously been described but to the best of our knowledge and belief no description of an O-transcarbamoylase has yet been made.

Microorganisms producing the O-transcarbamoylase may be chosen from cultures publicly available in culture collections, or may be isolated from appropriate natural sources, for example soils, sewages, sea waters, flowers, fruits, air or other sources by conventional means. The selection of a useful microorganism may readily be effected and the following procedure may, for example, be employed:

Microorganisms are grown under suitable conditions, e.g.

| Microorganism | Medium Composition | Cultivation |
|---|---|---|
| Bacteria | Meat Extract 1.8%<br>Peptone 1.0%<br>NaCl 0.5%<br>Tap Water<br>pH adjusted to 7.2<br>± 0.1 before autoclaving | 28°–37° C.<br>1–2 days |
| Fungi or Actinomycetes or Yeasts | Malt Extract 2.4%<br>Yeast Extract 0.5%<br>Tap Water<br>pH adjusted to 7.8<br>before autoclaving | 25°–28° C.<br>2–5 days |

The cells are harvested at various times during the fermentation by conventional means, e.g. centrifugation and washed with 10 mM piperazine-N,N'-bis(2-ethanesulphonic acid) (pipes) adjusted to pH 6.0 with sodium hydroxide. Packed cells (1 g) are resuspended in the same buffer (4.5 ml) and ruptured by a suitable method e.g. by stirring vigorously with glass beads or by sonication.

The broken cell suspension (40 $\mu$l) or the cell-free supernatant (40 $\mu$l), is added to carbamoyl phosphate (0.3 $\mu$moles), radioactive 3-hydroxymethyl cephalosporin (100 nCi (at about 2 Ci per mmole))e.g. [$^3$H]-7$\beta$-(5-amino-5-carboxypentanamido)-3-hydroxymethylceph-3-em-4-carboxylic acid, and preferably manganese chloride (100 nmoles), magnesium chloride (100 nmoles) and ATP (0.3 mmole) in a final volume of 0.1 ml water. This reaction mixture is incubated for 60 min at 28°.

Hydrochloric acid (1 M, 0.1 ml) is then added to lactonise the unchanged substrate. After 30 mins at 28°, 10 mM acetic acid (4.0 ml) followed by water (0.75 ml) containing Dowex-1 acetate (x8 200–400 Mesh) (0.5 ml packed volume) are added. After mixing, the Dowex-1 acetate is allowed to settle and the radioactivity in 2 ml of supernatant is measured in a liquid scintillation spectrometer (e.g. Packard Tricarb 3320) using 15 ml of dioxan based scintillation fluid (e.g. Nuclear Enterprises NE 250).

The presence of O-transcarbamoylase activity, and the extent thereof if it is found to be present, can be measured from the difference (>5%) between the radioactivity obtained from the incubation mixtures described and that obtained from incubation mixtures to which the hydrochloric acid is added immediately after the addition of the radioactive 3-hydroxymethyl cephalosporin. The formation of the 3-carbamoyloxymethyl cephalosporin is confirmed by suitable chromatographic analysis e.g. high pressure liquid chromatography (HPLC) of the reaction mixtures, preferably after lactonisation of the unchanged 3-hydroxy-methyl cephalosporin.

In the event of the cephalosporin substrate or product being degraded as evidenced by chromatography, a second alternative procedure may be employed. The broken cell suspension (50 $\mu$l) described above is added to (6R,7R)-3-hydroxymethyl-7-[2-methoxyimino-2-(fur-2-yl)acetamido]-ceph-3-em-4-carboxylic acid (syn isomer) (0.1 $\mu$mole), magnesium chloride (0.1 $\mu$mole), manganese sulphate (0.1 $\mu$mole), ATP (0.1 $\mu$mole), piperazine-N,N'-bis(2-ethane-sulphonic acid (6 $\mu$moles adjusted to pH 6.75 with KOH) and [$^{14}$C] carbamoyl-phosphate (50 nCi, 0.1 $\mu$mole) in a final volume of 0.1 ml water. The reaction is incubated at 28° for 10 min.

Hydrochloric acid (0.1 M, 0.9 ml) is then added followed by ethylacetate (1 ml). After mixing vigorously the emulsion is centrifuged (500 g for 1 min). A portion (0.5 ml) of the organic phase is dried under reduced pressure at 40° and the residue is mixed with water (0.5 ml). The radioactivity in the water is measured as described previously.

The presence of O-transcarbamoylase activity, and the extent thereof if it is found to be present, can be measured from the increase in radioactivity obtained from the incubation mixtures described over that from incubation mixtures in which the 3-hydroxymethylcephalosporin has been omitted. The formation of the 3-carbamoyloxymethylcephalosporin is confirmed by suitable chromatographic analysis e.g. hplc of the reaction mixtures preferably after lactonisation of the unchanged 3-hydroxymethylcephalosporin.

The O-transcarbamoylase may be derived from a species of the Order Actinomycetales, particularly from a species of the genus Streptomyces. Particularly suitable species which may be employed to provide the desired O-transcarbamoylase activity include *Streptomyces clavuligerus* for example strain NRRL 3585 as described in British Pat. No. 1,315,177; *Streptomyces wadayamensis,* for example strain ATCC 21984 as described in Dutch Patent Application No. 7308948; *Streptomyces albogriseolus,* for example strain NRRL 5735 as described in U.S. Pat. No. 3,914,158; *Streptomyces lactamdurans* for example strain NRRL 3802 as described in British Pat. No. 1,321,412; *Streptomyces jumonjinensis,* for example strain NRRL 5741 as described in British Pat. No. 1,387,965 and *Streptomyces lactamgenes,* for example the strain described in Japanese Patent Application No. 50/69294. Selectants or mutants of the strains mentioned above may also be employed.

A particularly preferred stain is *Streptomyces clavuligerus* NRRL 3585 or a selectant or mutant thereof.

As used herein, the term 'mutant' will include any mutant strain which arises either spontaneously or as a result of the action of an external agent, which may be either deliberately applied or otherwise. Mutant strains may be produced by a variety of methods including those outlined in Techniques for the Development of Micro-Organisms by H. I. Adler in "Radiation and Radioisotopes for Industrial Microorganisms," Proceedings of the Symposium, Vienna, 1973, p. 241, International Atomic Energy Authority. These methods include (i) Ionising radiation, for example X- and γ-rays, uv light, uv light in the presence of a photosensitising agent, for example 8-methoxypsoralen; nitrous oxide; hydroxylamine; pyrimidinc base analogues e.g. 5-bromouracil; acridines; alkylating agents e.g. ethyl methane sulphonate or mustard gas; hydrogen peroxide; phenols; formaldehyde; heat: and (ii) genetic techniques, such as recombination, transduction, transformation, lysogenisation, lysogenic conversion and selective techniques for spontaneous mutants.

As used herein, the term 'selectant' means a strain of the microorganism derived from a colony selected from the parent strain which has been cultivated in such a way as to provide a strain having one or more properties which are qualitatively or quantitatively different from those of the parent strain e.g. resistance to substances produced in fermentation. Such a selectant may, of course, be a spontaneous mutant of the parent microorganism but in some cases it may not be.

The O-transcarbamoylase may be prepared by culture of a microorganism which produces the enzyme in a nutrient medium therefor. The nutrient medium should contain sources of nitrogen, carbon and trace elements. The nitrogen source may, for example, be a conventional meat or yeast extract, peptone or a preparation such as tryptose, casein hydrolysate, whey powder or corn steep liquor. The source of carbon may for example be a carbohydrate source such as starch or any of its breakdown products, or other sugars, organic acids or paraffins. The optimal pH of the culture medium and the optimal cultivation temperature will depend upon the nature of the microorganism used. A desirable pH will usually be found in the range of pH 4 to 9 and the temperature will usually be in the range of 10° to 40° C. Cultivation of the microorganism will usually be carried out with stirring or shaking and aeration. The time at which the required enzymic activity reaches a maximum will vary according to the microorganism so the optimum cultivation time is desirably determined for each strain employed.

For microorganisms where the enzyme is extracellular, the liquid culture medium or the filtrate after removal of whole cells may be used as the source of enzyme. Where the enzyme is cell-bound it may be released for use by conventional methods such as sonication, grinding with glass beads or homogenisation, after suspension of cells in a suitable buffer. The resulting preparation, either with or without removal of cell debris, may be used as a source of enzyme. It is preferred, however, to purify the enzyme further by conventional means. Batch or column chromatography with ion-exchange celluloses or affinity adsorbents or other adsorbents e.g. hydroxylapatite may be employed. In addition, the enzyme may be concentrated or further purified by molecular sieve techniques e.g. ultrafiltration or by salting out. In general, during purification procedures, it is desirable to maintain the pH within the range 3–11. Such procedures will remove either partially or completely deleterious enzymes e.g. β-lactamases, amidohydrolases, carbamoyl phosphate kinases and phosphatases which might be present and which might interfere with the enzymic reaction or substrates. Various agents e.g. substrates, cofactors, metal ions, reducing agents or salts e.g. phosphates may desirably be used to improve the stability of the enzyme.

The enzyme may be employed in an immobilized form, e.g. by insolubilisation or entrappment thereof on or in a suitable matrix. Thus an extract of the enzyme may be covalently bound or linked to an otherwise inert inorganic or organic polymer, entrapped on or in a fiber, or on or in a membrane or polymer such as polyacrylamide gel, absorbed on an ion-exchange resin, cross-lined with a reagent such as glutaraldehyde, or occluded in an envelope such as a bead. Immobilized O-transcarbamoylases of these types may advantageously be employed both in batch processes after which the enzyme may be reused, and continuous flow processes wherein substrates pass through a column containing the immobilized enzyme.

In another aspect of this invention, we provide a process for the preparation of a 3-carbamoyloxymethyl cephalosporin in which a 3-hydroxymethyl cephalosporin is contacted with a carbamoyl compound or a precursor therefor in the presence of an enzyme showing the desired O-transcarbamoylase activity derived from a microbial source.

The preferred carbamoyl compound is carbamoyl phosphate ($NH_2CO.OPO_3H_2$), though other carbamoyl compounds e.g. carbamoyl aspartate or carbamoyl oxamate and precursors such as citrulline, or a mixture of ATP, bicarbonate and either ammonia or glutamine may also be used. The carbamoyl phosphate may be generated from inorganic precursors, e.g. by the combination of an alkali metal phosphate e.g. potassium phosphate and an alkali metal isocyanate e.g. potassium isocyanate.

The cephalosporin substrate may have the formula

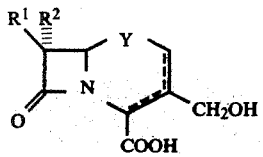
(I)

wherein $R^1$ is an amino or blocked amino group, for example a $C_{1-20}$ carboxylic acylamido group; $R^2$ is a hydrogen atom or a lower alkyl, (e.g. methyl, ethyl and propyl), lower alkoxy (e.g. methoxy, ethoxy, propoxy), lower alkylthio (e.g. methylthio, ethylthio) or lower alkanoyl (e.g. acetyl) group (the term "lower" as used designating groups containing not more than 8, preferably not more than 6 carbon atoms); Y represents a group >S or >S→O and the dotted line bridging the 2, 3 and 4 positions indicates that the compound may be a ceph-2-em or ceph-3-em compound; together with salts or esters thereof. Suitable carboxylic acylamido groups will be those conventionally found in cephalosporin antibiotics, such as are derived from amide forming acyl groups found in the literature pertaining to cephalosporin compounds.

Particular acylamido groups which may be present include groups of the formula

where R is a carbocyclic or heterocyclic aryl group (e.g. phenyl; phenyl substituted by one or more of halo, hydroxy, lower alkyl, nitro, amino, lower alkanoyl, lower alkoxy or lower alkylthio; thienyl or furyl) or an aryloxy, arylthio, aryl lower alkoxy or aryl lower alkylthio group (e.g. phenoxy, phenylthio, 5-methyl-1,3,4,-thiadiazol-2-ylthio or benzylthio) and k is an integer of from 1 to 4; a group of formula

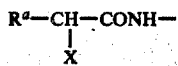

where $R^a$ is an aryl group (e.g. a monocyclic or bicyclic carbocyclic or heterocyclic aryl group such as phenyl, naphthyl or phenyl substituted by one or more of halo, hydroxy, lower alkyl, nitro, amino, lower alkanoyl, lower alkoxy or lower alkythio) and X is amino, protected amino (e.g. containing any of the N-protecting groups discussed below in connection with the D-5-amino-5-carboxypentanamido group, for example a t-butoxycarbonyl group), carboxy, carbalkoxy or hydroxy; and a group of formula

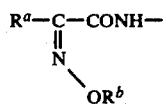

where $R^a$ has the above-defined meaning (e.g. where $R^a$ is phenyl, substituted phenyl, naphthyl, thienyl, furyl or pyridyl), and $R^b$ is hydrogen, acyl (e.g. lower alkanoyl), lower alkyl (e.g. methyl, ethyl, propyl or butyl), cycloalkyl (e.g. containing 5-7 carbon atoms, such as cyclopentyl or cyclohexyl), aryl (e.g. carbocyclic aryl such as phenyl), aryl lower alkyl (e.g. benzyl or phenethyl), or a group of formula

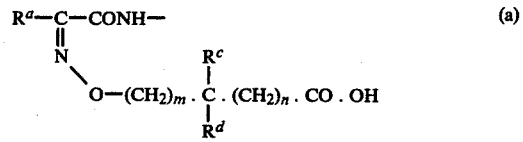
(a)

[wherein $R^a$ represents a thienyl or furyl group and $R^c$ and $R^d$, which may be the same or different are each selected from hydrogen, $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, naphthyl, thienyl, furyl, carboxy, $C_{2-5}$ alkoxycarbonyl (e.g. ethoxycarbonyl) and cyano, or $R^c$ and $R^d$ together with the carbon atom to which they are attached form a $C_{3-7}$ cycloalkylidene or cycloalkenylidene group (e.g. a cyclobutylidene, cyclopentylidene or cyclohexylidene group); and m and n are each 0 or 1 such that the sum of m and n is 0 or 1], or a group of formula

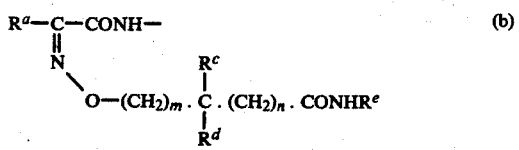
(b)

[wherein $R^a$ represents a phenyl, thienyl or furyl group and $R^c$, $R^d$, m and n are as defined above and $R^c$ and $R^d$ may additionally represent an aminocarbonyl or N-substituted aminocarbonyl [e.g. N-($C_{1-4}$ alkyl)aminocarbonyl such as N-methylaminocarbonyl] group and $R^e$ is hydrogen or $C_{1-4}$ alkyl (e.g. a methyl, ethyl, propyl, isopropyl or t-butyl) group.]

Examples of $R^1$ groups falling within the above general formulae which may be present in compounds of formula I include phenylacetamido, thienylacetamido, 2-hydroxy-2-phenylacetamido, 2-t-butoxycarbonylamino-2-phenylacetamido and syn-2-furyl-2-methoxyiminoacetamido.

Other acylamido groups $R^1$ which may be present in the compounds of formula I include the D-5-amino-5-carboxypentanamido group found in naturally-occuring fermentation-produced compounds such as cephalosporin C; N-protected derivatives of the D-5-amino-5-carboxy-pentanamido group, e.g. wherein the amino group is substituted by a protecting group of the type described in any of British Patent Specification Nos. 1,041,985; 1,302,015 or 1,313,207; an acylamido group obtained by transformation of the D-5-amino-5-carboxypentanamido group, e.g. a 4-carboxybutamido group obtained therefrom by, for example, enzymic deamination and oxidation described for example in British Pat. No. 1,272,769; and a formamido group.

In the process of the invention, the substrates may be combined and incubated with a preparation of the enzyme of the invention, desirably in buffer solution, at, for example, 0°-60° C. preferably 20°-40° C., e.g. about 28° C. at a pH preferably in the range 4-9, e.g. from 5 to 8. The reaction is preferably carried out in the presence of divalent metal ions such as those of calcium, magnesium, zinc, copper, iron, manganese and cobalt, for example, from 1 µM to 10 mM in concentration, e.g. about 1.0 mM manganous ions together with about 1.0 mM magnesium ions, and if desired a cofactor such as ATP e.g. at a concentration of from 50 µM to 150 mM. When the reaction is complete i.e. when the cephalosporin substrate is no longer converted to product, as judged by chromatography of the reaction mixture, the desired 3-carbamoyloxymethyl cephalosporin is recovered after, for example, acidification and centrifugation to remove the enzyme preparation, by suitable extraction and purification procedures, e.g. by the use of solvents or ion exchange chromatography.

The hydroxymethyl cephalosporin substrate may be formed in situ from a 3-lower alkanoyloxymethyl cephalosporin such as a 3-acetoxymethyl cephalosporin by means of an esterase in the reaction medium which is capable of converting the alkanoyloxymethyl cephalosporin to a hydroxymethyl cephalosporin.

The invention will now be more particularly described in the following Preparations and Examples which should not be construed as limiting the invention. Throughout the Examples all temperatures are in °C.

PREPARATION 1

[3-Methyl-$^3$H]-7β-(D-5-amino-5-carboxypentanamido)-3-methyl-ceph-3-em-4-carboxylic acid Potassium cephalosporin C (485 mg), palladium oxide on kieselguhr (616 mg) and water (7 ml) were mixed in a reactor. The reactor was purged with nitrogen gas for 10 minutes and then filled with tritium gas. Triethylamine (0.2 ml) was added and the mixture stirred vigorously at 20° C. for 1 hour. During this period approximately 6 Ci of tritium were taken up. The flask was purged with nitrogen and the contents filtered on a kieselguhr bed supported on a 3 cm sinter. The bed was washed with water and the filtrate evaporated to a brown oily sludge.

100 mCi of this preparation in water (25 ml) was adjusted to pH 2.8 with dilute hydrochloric acid and carbon (SS110-150 mg) was added. The suspension was stirred (30 minutes) and then filtered on a kieselguhr bed. The bed was washed with water (10 ml) and the title compound eluted from the carbon with an acetone-water mixture (1:2 by volume). The eluate was then applied to a 0.5 ml column of IRA-68 acetate and after washing the column with water the title compound was eluted from the column with potassium acetate solution (1% w/v, 50 ml). The yield at this stage was 50 mCi. 20 mCi of this solution was desalted using the carbon treatment described above. The carbon eluate was evaporated under reduced pressure, and the title compound it contained was purified by preparative thin layer chromatography on cellulose using propan-1-ol:water:acetic acid (5:2:1 by volume) as solvent. The zone visualised by quenching under ultra-violet light (254 mn) was eluted into potassium acetate solution (0.1% w/v) and the title compond (5.4 mCi), which showed a specific activity of about 2.5 Ci/mmole, was recovered.

PREPARATION 2

[3-Hydroxymethyl-$^3$H]-7β-(D-5-amino-5-carboxypentanamido)-3-hydroxymethylceph-3-em-4-carboxylic acid (desacetyl cephalosporin C)

(a) Preparation of dioxygenase enzyme:

Acremonium chrysogenum Brotzu strain CMI 49137, which is fully described by W. Gams in Cephalosporin-artige Schimmelpilze (Hyphomycetes) (1971), pp. 109-111 was grown on agar slopes containing per liter of water:
Maltose: 40 g
Oxoid malt extract: 24 g
Oxoid peptone: 10 g
Agar: 20 g The slopes were incubated for 7 days at 28° C. and half of each slope harvested and inoculated into flasks containing 40 ml of a medium comprising per liter of water:
Corn steep liquor: 25 ml
Ammonium acetate: 5.5 g
Sucrose: 25 g
Calcium carbonate: 5 g The flasks were incubated on an orbital incubator at 28° C. for 48 h. and portions (1.25 ml) of this culture were then used to inoculate flasks containing 25 ml of a medium comprising per liter of water:
Soya bean meal: 36 g
Lactose: 38 g
Calcium carbonate: 10 g
Ammonium sulphate: 5 g
Urea: 0.6 g
L-methionine 1.9 g
Maize oil: 3.0 g The flasks were incubated at 28° C. on an orbital incubator for 72 h. and the final culture (2 liters) harvested by centrifugation at 4000 G for 2 minutes at 4° C. The mycelium was scraped away from the calcium carbonate layer and washed in cold potassium phosphate buffer (0.01 M, pH 7.0). The washed mycelium (40 g) was made up to 180 ml with the same buffer containing 2-oxoglutarate (2 mM) and ascorbic acid (2 mM) and broken by stirring for 1 minute with glass beads (250 ml, 1 mm diameter) in a Dyno Mill running at 2000 rpm and cooled with brine at −5°. The broken cell preparation was centrifuged (30,000 G, 30 min) and the supernatant concentrated to 5 ml by ultra-filtration to give a preparation with a dioxygenase activity of approximately 1.5 nmoles/min/ml.

(b) Purification of dioxygenase:

A concentrated supernatant (100 ml) containing dioxygenase (activity 0.92 nmole/min/ml., specific activity about 0.076 nmole/min/mg protein) was dialysed against phosphate buffer (10 mM, pH 7.0) containing 7β-(D-5-amino-5-carboxypentanamido)-3-methylceph-3-em-4-carboxylic acid (0.2 mM) and dithiothreitol (0.1 mM) and applied to a column of DEAE cellulose (DE23, 100 g wet weight) equilibrated with the dialysing buffer. The dioxygenase was eluted with a linear gradient of sodium chloride (1.5 liters, 0-1 M) in the dialysing buffer. The fractions were assayed for dioxygenase activity as follows:

Portions of the fractions (40 µl) were added to reaction mixtures containing [3-methyl-$^3$H]-7β-(D-5-amino-5-carboxypentanamido)-3-methylceph-3-em-4-carboxylic acid (14 nmoles, approx. 2 Ci/mole), 2-oxoglutarate (70 nmoles), ascorbate (70 nmoles) and pipes [piperazine-N,N'-bis(2-ethane sulphonic acid)] (7 µmoles) buffered to pH 7.0 with potassium hydroxide in a final volume of 70 µl. The reaction mixtures were incubated at 28° C. for 60 minutes. An equal volume of Mhydrochloric acid was then added and the mixture incubated at 28° C. for 30 minutes. A portion (20 µl) of each sample was then applied to the top of a Dowex-1 acetate column (25 mm×4 mm), the columns washed with water (2×2.5 ml) and the eluates made up to 6 ml. A portion (2 ml) of each of these solutions was added to dioxan based scintillation liquid (15 ml) and the radioactivity counted on a scintillation spectrometer. The amount of dioxygenase activity present was measured from the difference in the radioactivity obtained from the incubation mixtures described and that obtained from an incubation mixture to which the hydrochloric acid was added immediately after addition of radioactive 3-methyl cephalosporin.

The most active fractions, which were eluted at a sodium chloride concentration of about 0.5 M, were pooled and concentrated to 5.2 ml by ultra-filtration (Diaflo UM 10 membrane at 30 psi) and dialysed against phosphate buffer (10 mM, pH 7.0) containing dithiothreitol (0.1 mM). Dioxygenase with an activity of 62 nmole/min was recovered. The specific activity was about 3.3 nmole/min/mg protein.

(c) [3-Methyl-$^3$H]-7$\beta$-(D-5-amino-5-carboxypentanamido)-3-methylceph-3-em-4-carboxylic acid (1.25 $\mu$moles, 12.0 mCi) was incubated for 7 hr at 37° with dioxygenase (20 nmole/min), purified as described in part (b) above, ascorbic acid (100 $\mu$moles), 2-oxoglutarate (100 $\mu$moles) ferric ions (1 ml of water saturated with ferric ammonium sulphate) and pipes buffer (0.5 mmoles, pH 7.0) in a final volume of 10 ml.

Acetic acid (2 ml) was then added and the reaction mixture centrifuged. The supernatant was dried under reduced pressure, the residue dissolved in water (20 ml), and applied to a column of DEAE cellulose (20 g wet weight) equilibrated with potassium phosphate buffer (10 mM pH 7.0). The column was eluted with a linear gradient of sodium chloride (200 ml 0–0.02 M) in phosphate buffer (10 mM, pH 7.0). Fractions containing title compound, which eluted at about 0.1 M sodium chloride, were pooled, concentrated under reduced pressure and fractionated on a column of Biogel P2 (1000 mm×25 mm diam.). The cephalosporins which were detected by their absorption at 260 nm, were collected and analysed by t.l.c. and h.p.l.c. Only title compound (2.28 mCi) could be detected in the product.

EXAMPLE 1

Preparation of extract of O-transcarbamoylase

A sporulated slope of *Streptomyces clavuligerus* NRRL 3585 was suspended in sterile water (10 ml) and a portion (2.5 ml) inoculated into Medium I, [a solution containing sucrose (20 g), soya bean meal (Bibby's) (15 g), yeast extract (Oxoid) (5 g), dipotassium hydrogen phosphate (0.2 g) Oxoid tryptone (5 g), glycerol (10 g) and tap water (1000 ml)] (25 ml in 250 ml baffled shake flask). This culture was incubated for 48 hours at 26° C. in an orbital incubator and a portion (0.25 ml) of the culture then used to inoculate Medium II, [a solution containing sodium citrate (2 g), dipotassium hydrogen phosphate (1.4 g), potassium dihydrogen phosphate (0.6 g), MgSO$_4$.7H$_2$O (0.5 g), FeSO$_4$.7H$_2$O (0.25 g), L-asparagine (0.2 g), soluble starch (1.0 g) and distilled water (1000 ml)] (25 ml in 250 ml shake flask). This culture was then incubated for 48 hours at 26° and the cells then harvested by centrifugation (18,000 rpm for 15 minutes at 4°). The cells were resuspended in pipes buffer (5 ml, 10 mM, pH 6.0) and were disrupted at 4° using an MSE 568 Ultrasonicator at maximum amplitude for 5 minutes.

EXAMPLE 2

Synthesis of 7$\alpha$-methoxy-7$\beta$-(D-5-amino-5-carboxypentanamido)-3-carbamoyloxymethylceph-3-em-4-carboxylic acid (cephamycin C) from [$^{14}$C] carbamoyl phosphate and 7$\alpha$-methoxy-7$\beta$-(D-5-amino-5-carboxypentanamido)-3-hydroxymethylceph-3-em-4-carboxylic acid (7$\alpha$-methoxy desacetylcephalosporin C) in the presence of the O-transcarbamoylase from *Streptomyces clavuligerus*

Radioactive [$^{14}$C] carbamoyl phosphate (31 nmoles, 0.25 $\mu$Ci) and 7$\alpha$-methoxydesacetyl cephalosporin C (100 $\mu$g) were incubated with a portion (1 ml) of the O-transcarbamoylase preparation from Example 1 for 30 minutes at 27°.

The reaction mixture was cooled on ice and unlabelled cephamycin C (50 $\mu$l of 20 mg/ml) was added as a 'carrier' for any radioactive cephamycin C formed. This was followed by the addition of acetic acid (0.25 ml of 5 M at 4°). The precipitate was centrifuged off and the supernatant evaporated to dryness under reduced pressure.

The dried supernatant was resuspended in buffer [formic/acetic acid (0.06 M acetic acid adjusted to pH 2.5 with formic acid)] (35 $\mu$l) and applied (30 $\mu$l) to an anionic exchange HPLC column (Zipax SAX, 2.5×100 mm, at 1,000 psi with a flow rate of 1 ml/min) equilibrated in the same buffer. The major E$_{266}$ peak containing cephamycin C was collected (5 ml), evaporated to dryness and again taken up in the above buffer (35 $\mu$l). This was then applied (30 $\mu$l) to a cationic HPLC column (Zipax SCX, 2.5×100 mm at 1,000 psi with a flow rate of 1 ml/min) and fractions covering the peak of cephamycin C collected. The bulked fractions were adjusted to 3 ml with distilled water and their E$_{266}$ and radioactivity determined.

The radioactivity incorporated into cephamycin C was calculated as being 0.7%, after correcting for a 5% recovery of the carrier.

EXAMPLE 3

O-Transcarbamoylation reaction: Use of cell-free supernatants

The procedure followed was similar to that of Example 2 except that the cell homogenate was replaced by the cell-free supernatant obtained when the homogenate is centrifuged at 30,000 g for 10 min at 4°.

The radioactivity incorporated into cephamycin C was calculated as being 0.26% after correcting for the recovery of carrier (about 5%).

EXAMPLE 4

Synthesis of cephamycin C from 7$\beta$-(D-5-amino-5-carboxypentanamido)-7$\alpha$-methoxy-3-acetoxymethylceph-3-em-4-carboxylic acid (7$\alpha$-methoxy cephalosporin C) in the presence of an acetyl esterase and the O-transcarbamoylase from *Streptomyces clavuligerus*

(a) The procedure followed was similar to that of Example 2 except that 7$\alpha$-methoxy cephalosporin C (100 $\mu$g) was used. Chromatographic analysis of the total reaction mixture after the incubation showed that the bulk of the 7$\alpha$-methoxy cephalosporin C had been converted to 7$\alpha$-methoxy desacetyl cephalosporin C by the esterase known to be present in extracts of *S.*

*clavuligerus* (Brannon, D. R., Fukuda, D. S., Mabe, J. A., Huber, F. M. and Whitney, J. G. (1972), Antimicrobiol Agents Chemother., 1, 237)

The radioactivity incorporated into cephamycin C was calculated as being 0.12% after correcting for the recovery of carrier (about 5%). (b) The procedure followed was similar to that of (a) above except that [carbamoyl-$^{14}$C] citrulline (8 nmoles, 0.5 μCi) was used in place of the carbamoyl phosphate.

The radioactivity incorporated into cephamycin C was calculated as being 0.07% after correction for the recovery of carrier (about 5%).

EXAMPLE 5

(6R,7R)-3-Carbamoyloxymethyl-7-[2-methoxyimino-2-(fur-2-yl) acetamido] ceph-3-em-4-carboxylic acid (syn isomer)

*S. clavuligerus* NRRL 3585 was grown in broth (1.2 liters) and harvested as described in Example 1. The cells were washed with 10 mM imidazole buffer adjusted to pH 7.0 with HCl. The wet cells (45 g) were resuspended in the imidazole buffer (180 ml) and were stirred for 1 min with 0.1 mm glass beads in a Dyno Mill running at 2000 rpm and cooled with brine at −5° C. Th broken-cell homogenate was centrifuged (30.000 g. 30 min) and the supernatant was applied to a column containing DEAE cellulose (100 g wet weight) equilibrated with the imidazole buffer. The 0-transcarbamoylase was eluted with a sodium chloride gradient (0–1 M) in 10 mM imidazole pH 7.0. The combined fractions (90 ml) which eluted at about 0.5 M sodium chloride and which contained the 0-transcarbamoylase were concentrated to 6 ml by ultrafiltration.

Concentrated enzyme (0.5 ml) was incubated at 28° in a final volume of 1.0 ml water containing (6R,7R)-3-hydroxymethyl-7-[2-methoxyimino-2-(fur-2-yl) acetamido]ceph-3-em-4-carboxylic acid (syn-isomer) (0,1 μmole), carbamoyl phosphate (3 μmoles), ATP (1 μmole), magnesium chloride (1 μmole), manganese chloride (1 μmole) & pipes buffer (50 μmoles) adjusted to pH 6.0 with potassium hydroxide. After 2 hr the reaction was stopped by the addition of acetic acid (20 μl). The pH was then adjusted to 2.0 with M hydrochloric acid and the precipitated protein was centrifuged off. The supernatant was extracted with ethylacetate (2.5 ml). The organic phase was collected and evaporated to dryness. The cephalosporins it contained were then separated by hplc [100 mm × 5 diam. column Partisil 5 eluted at 1500 psi with chloroform:methanol:90% formic acid (25:2:1 v/v) saturated with water] and were detected by their absorption at 270 nm. Their retention time was compared with standard samples. The size of the U.V. absorbing peaks showed that 20% of the cephalosporin starting material had been converted to title compound.

EXAMPLE 6

0-Transcarbamoylation reaction: Synthesis of 7β-(D-5-amino-5-carboxypentanamido)-3-carbamoyloxymethyl-ceph-3-em-4-carboxylic acid (cephalosporin C carbamate) from desacetyl cephalosporin C and carbamoyl phosphate (a) In the presence of a limiting concentration of ATP.

Carbamoyl phosphate (0.3 μmoles), [3-hydroxymethyl-$^{3}$H] desacetyl cephalosporin C (250 nCi, 0.025 nmoles), manganese chloride (0.1 nmole), magnesium chloride (0.1 μmole), glutamine (0.1 μmole), sodium bicarbonate (0.2 μmole) and ATP (0.1 nmole) were mixed in a final volume of 0.1 ml with 40 μl of the sonicated cell suspension described in Example 1. The mixture was incubated at 28° for 60 min. The reaction was stopped with M hydrochloric acid (0.1 ml).

The acidified reaction mixture was incubated at 28° for 30 min to lactonise the desacetyl cephalosporin C. The mixture was then diluted with 10 mM acetic acid (4.0 ml) and 1 ml was chromatographed on a column (25 mm × 6 mm) of Dowex-1 acetate (×8 200–400 mesh). The column was washed with 10 mM acetic acid (4 ml) and the radioactivity in the eluate was determined.

The amount of cephalosporin C carbamate formed was estimated from the reduction in the radioactivity eluted from the column compared to that eluting when similar incubation mixtures were treated with hydrochloric acid immediately after the addition of the radioactive labelled desacetyl cephalosporin C. 12% of the desacetyl cephalosporin C was converted to cephalosporin C carbamate.

Chromatographic analysis (cellulose-TLC using N-propanol: acetic acid:water, 5:1:2) of the reaction mixture after the addition of the acid confirmed the synthesis of cephalosporin C carbamate. Radioactivity in spots running with cephalosporin C carbamate and the lactone of desacetyl cephalosporin C confirmed that 12% of the desacetyl cephalosporin C had been converted to cephalosporin C carbamate.

(b) In the presence of a saturating concentration of ATP.

The procedure followed was similar to that of (a) above except that 1 nmole of radioactively labelled desacetyl cephalosporin C and 10 nmoles ATP were used.

56% of desacetyl cephalosporin C was converted to cephalosporin C carbamate.

EXAMPLE 7

Synthesis of [$^{3}$H]-7β-(D-5-amino-5-carboxypentanamido)-3-carbamoyloxymethylceph-3-em-4-carboxylic acid Supernatant (50 μl) prepared as in Example 3 from broken cells of *S. clavuligerus* NRRL 3585 was incubated at 28° for 30 min in a total volume of 0.1 ml water which also contained [3-hydroxymethyl-$^{3}$H]-7β-(D-5-amino-5-carboxypentanamido)-3-hydroxymethylceph-3-em-4-carboxylic acid (1 nmole, 0.25 μCi), ATP (100 nmoles), magnesium chloride (100 nmoles), manganese chloride (100 nmoles) and the compounds shown in the Table.

M Hydrochloric acid (0.1 ml) was added to stop the reaction and to lactonise the unreacted cephalosporin starting material. After 30 min at 28° water (4.0 ml) containing Dowex-1-acetate (0.33 ml packed volume AG1×8 200–400 mesh) was added. The radioactivity in the supernatant due to the lactonised cephalosporin starting material was measured in the presence of a dioxan-based liquid scintillator (Nuclear Enterprises NE250). The activity of the 0-transcarbamoylase was calculated from the drop in radio-activity compared to a sample in which the supernatant was replaced by 50 μl water.

| Compound added to incubation mixture | 0-transcarbamoylase activity in the supernatant (nmoles/min/ml) |
|---|---|
| None | 0.02 |
| Carbamoyl phosphate (300nmoles) | 0.34 |
| Potassium phosphate (300nmoles phosphate at pH7) and potassium cyanate (300nmole) | 0.16 |

EXAMPLE 8

Preparation of 0-transcarbamoylase from *S. clavuligerus*

An actively growing culture of *S. clavuligerus* NRRL 3585 (6 liters) was used to inoculate the following medium (150 liters) adjusted to pH 7.0 with potassium hydroxide:

|  | Wt. in g/liter |
|---|---|
| glycerol | 35 |
| citric acid | 1.5 |
| L-asparagine | 6.7 |
| MgSO$_4$ . 7H$_2$O | 0.5 |
| K$_2$HPO$_4$ | 0.42 |
| CaCl$_2$ | 0.2 |
| NaCl | 0.1 |
| ZnSO$_4$ . 7H$_2$O | 0.05 |
| FeSO$_4$ . 7H$_2$O | 0.03 |
| MnSO$_4$ . 4H$_2$O | 0.1 |
| piperazine-N,N'-bis(2-ethane sulphonic acid) | 0.02 |

The culture was grown for 45 hours at 28° C. with an aeration rate of 10 cu.ft/min and no stirring.

The cells were then harvested at a flow rate of 200 liters/hour in a continuous flow centrifuge and resuspended in 10 mM imidazole buffer adjusted to pH 6.8 with hydrochloric acid (20 liters). The preparation was broken at a flow rate of 120 ml/min. by stirring at 3,000 rpm with 500 ml of glass beads (0.1 mm diameter) in a Dynomill fitted with a 0.6 liter continuous-flow head.

The 0-transcarbamoylase was absorbed from this preparation with DEAE cellulose (2×4 kg; equilibrated in 10 mM imidazole buffer, pH 6.8). The DEAE cellulose was washed with the same buffer (2×8 liters) and then with buffer containing 0.1 M sodium chloride (2×8 liters) and finally the enzyme was eluted with buffer containing 0.5 M sodium chloride (3×8 liters). All these and subsequent treatments were at 4°. Solid ATP and carbamoyl phosphate were added to the eluate to bring the concentration of each to 0.1 mM. This preparation was treated twice with a slurry of hydroxylapatite (2 liters; 1:1 (v/v) settled bed hydroxylapatite to 5 mM potassium phosphate equilibrating buffer, pH 6.8) to absorb unwanted protein. The enzyme was precipitated from the supernatant with ammonium sulphate (9.6 kg) in a stainless steel churn then redissolved in imidazole buffer (500 ml) containing 0.5 M sodium chloride. The enzyme was finally dialysed against changes of imidazole buffer (2×10 liters) containing 0.5 M sodium chloride, 0.01 mM carbamoyl phosphate and 0.1 mM ATP to afford a dialysed concentrated solution of 0-transcarbamoylase containing about 30 international units.

EXAMPLE 9

(6R,7R)-3-Carbamoyloxymethyl-7-[2(fur-2-yl)-2-methoxyiminoacetamido]ceph-3-em-4-carboxylic acid (syn isomer)

(i) (6R,7R)-3-Hydroxymethyl-7-[2-(fur-2-yl)-2-methoxyiminoacetamido]ceph-3-em-4-carboxylic acid (syn isomer) (40 mg), ATP (300 mg), carbamoyl phosphate (150 mg), magnesium sulphate (20 mg) and manganese chloride (20 mg) were added to a portion of the 0-transcarbamoylase solution (50 ml) prepared in Example 8 and the final volume made up to 100 ml at a pH of 6.75. The mixture was incubated at 28° for 3 hours and was then acidified by addition of conc. hydrochloric acid (2.5 ml), left for 10 mins. and extracted with ethyl acetate. The ethyl acetate layer was back extracted with 0.1 M sodium bicarbonate which was then acidified and re-extracted with ethyl acetate. This extract was dried under reduced pressure and the solid triturated with diethyl ether to afford title compound (15.3 mg) as a dry powder, $\hat{E}_{1\ cm}^{1\%}$ 405 (273 nm). The n.m.r. spectrum resembled that of an authentic sample of title compound.

(ii) The process was repeated with ammonium (6R,7R)-3-acetoxymethyl-7-[2-(fur-2-yl)-2-methoxyiminoacetamido]ceph-3-em-4-carboxylate (syn isomer) (40 mg) as substrate and with the addition of pig liver acetylesterase (1 unit). Analysis of the product by TLC (silicachloroform/methanol/90% formic acid - 90:16:4) showed the presence of a new u.v. absorbing spot with an identical R$_f$ to the standard sample of title compound.

EXAMPLE 10

The process of Example 9 (i) was repeated with 3-hydroxymethylceph-3-em-4-carboxylic acid substrates having the 7-acylamido groups shown in Table I to yield the corresponding 3-carbamoyloxymethylceph-3-em-4-carboxylic acid.

Table I

| 7-Acylamido group | Wt of substrate | Yield of product | $E_{1cm}^{1\%}$ of product |
|---|---|---|---|
| phenylacetamido | 40 mg of 52% pure free acid | 15 mg | 187 (260nm) |
| thienylacetamido | 40 mg of free acid | 22 mg | 209 (259nm) |

The n.m.r. spectra of the products resembled those of authentic samples of the appropriate 3-carbamoyloxymethylceph-3-em-4-carboxylic acids.

EXAMPLE 11

7-Amino-3-carbamoyloxymethylceph-3-em-4-carboxylic acid 7-amino-3-hydroxymethylceph-3-em-4-carboxylic acid (40 μg), [$^{14}$C] carbamoyl phosphate (150 μg, 7.5 μCi), magnesium sulphate (20 μg), manganese chloride (20 μg) and pipes buffer (0.5 μmole, pH 6.75) were incubated with 0-transcarbamoylase as described in Example 9(i). After incubation the mixture was acidified with glacial acetic acid (10 μl), clarified by centrifugation and the supernatant dried by rotary evaporation. This material was taken up in acetate/formate buffer [glacial acetic acid (5 ml), formic acid (0.2 ml) in methanol/water (40:60 v/v, 1 liter), pH adjusted to 3.9 with 4 N sodium hydroxide] (30 μl) and a portion (10

μl) was applied to a Partisil 10 SAX column (250 mm×4.6 mm) and eluted with the same buffer at 100 psi (1 ml/minute). The U.V. absorption at 260 nm and radioactivity of the eluate were monitored. A new U.V. absorption peak was detected after 12 minutes which also contained radioactivity. This peak corresponded to that obtained with authentic title compound. The conversion of cephalosporin starting material into title compound was 13%.

We claim:

1. An 0-transcarbamoylase of microbial origin which is capable of transferring a carbamoyl group to a 3-hydroxymethyl cephalosporin to produce a 3-carbamoyloxymethyl cephalosporin, and which is partially or completely free from deleterious enzymes.

2. The 0-transcarbamoylase of claim 1 which is derived from a species of the Order Actinomycetales.

3. The 0-transcarbamoylase of claim 2 which is derived from a species of the genus Streptomyces.

4. The 0-transcarbamoylase of claim 3 which is derived from a strain selected from the group consisting of *Streptomyces clavuligerus, Streptomyces wadayamensis, Streptomyces lactamdurans, Streptomyces albogriseolus, Streptomyces jumonjinensis, Streptomyces lactamgenes*, and a selectant or mutant thereof.

5. The 0-transcarbamoylase of claim 4 which is derived from *Streptomyces clavuligerus* strain NRRL-3585 or a selectant or mutant thereof.

6. The 0-transcarbamoylase of claim 1 free from β-lactamases, amidohydrolases, carbamoyl phosphate kinases and phosphatases.

* * * * *